United States Patent [19]
Collins et al.

[11] Patent Number: 4,617,411

[45] Date of Patent: Oct. 14, 1986

[54] 3-OXAPROSTAGLANDINS

[75] Inventors: Paul W. Collins, Deerfield; Richard M. Weier, Lake Bluff, both of Ill.

[73] Assignee: G. D. Searle & Co., Skokie, Ill.

[21] Appl. No.: 715,445

[22] Filed: Mar. 25, 1985

Related U.S. Application Data

[62] Division of Ser. No. 558,471, Dec. 6, 1983, Pat. No. 4,529,812.

[51] Int. Cl.$^4$ .................................................. C07F 7/18
[52] U.S. Cl. .................................................... 556/443
[58] Field of Search ......................................... 556/443

[56] References Cited

U.S. PATENT DOCUMENTS 4,254,285  3/1981  Wissner .............................. 568/379

Primary Examiner—Robert Gerstl
Attorney, Agent, or Firm—John J. McDonnell

[57] ABSTRACT

This invention relates to novel 3-oxa-15-desoxy-16-hydroxy-16-alkyl prostaglandins of the $E_2$ series and the 5,6-acetylene derivatives thereof. These compounds are useful for their gastric antisecretory, cytoprotective, antiulcer, and antihypertensive activity. In addition the invention also discloses certain novel trialkylsilyl acetylenic intermediates.

2 Claims, No Drawings

3-OXAPROSTAGLANDINS

This is a division, of application Ser. No. 06/558,471, filed Dec. 6, 1983 now U.S. Pat. No. 4,529,812.

BACKGROUND OF INVENTION

The present invention relates to certain novel organic compounds. In particular this invention relates to certain novel 3-oxaprostaglandin derivatives of Formula VII. In addition, this invention relates to certain trialkylsilyl intermediates of Formula VIII.

The novel compounds of the present invention display valuable pharmacological properties as is exemplified by their ability to inhibit the gastric secretion stimulated by secretogogues such as histamine and pentagastrin. In addition, these compounds possess the remarkable ability to protect the gastric and intestinal mucosa against the damaging effects of such agents as ethanol and aspirin. This effect has been termed "cytoprotection" (see A. Robert et al., *Gastroenterology,* 77, 433 (1979)). Furthermore, these compounds have the surprising advantage of substantially decreased undesirable side effects such as diarrhea and uterine stimulant activity displayed by related substances. The gastric antisecretory activity is determined by standard laboratory means.

Gastric antisecretory agents may be used to treat such diseases as hypersecretion of gastric acid and peptic ulcer. A number of methods to control these conditions exist including, gastric antacids, antimuscarinic drugs, $H_2$-receptor blockers and prostaglandins (PG). Goodman and Gilman, Sixth Ed., 1980, pgs. 997, 632, 995–997 and 678.

PG analogs are all known to cause side effects, notably diarrhea. However, the capacity to suppress gastric secretion by these compounds is well documented.

Prostanoic acid is well known and has the structure and numbering as follows.

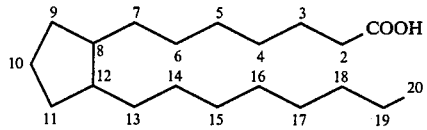

The compounds are more particularly derivatives of $PGE_2$. For background on prostaglandins, see for example Bergstrom et al., *Pharmacol. Rev.* 20, 1 (1968).

PRIOR ART

Derwent abstract 60337V/34 corresponding to German Offenlegungsschrift 2,406287 depicts 3-oxaprostaglandins of the $E_2$ series, specifically as 15-hydroxy compounds.

SUMMARY OF THE INVENTION

The present invention particularly provides a compound according to formula:

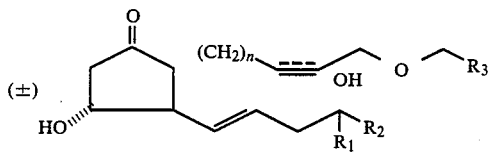

Wherein $R_1$ is:
(a) hydrogen;
(b) alkyl of 1 to 6 carbon atoms, inclusive;
(c) trifluoromethyl;
(d) trichloromethyl;
(e) alkenyl; or
(f) alkynyl;

wherein $R_2$ is straight chain alkyl of 1 to 6 carbon atoms inclusive; wherein $R_3$ is:
(a) —$COOR_4$;
(b) —$CH_2OH$; or
(c) —$C(O)CH_2OH$;

wherein $R_4$ is alkyl of 1 to 6 carbon atoms inclusive and wherein n is an integer of from 1 to 6 inclusive.

In addition the invention also relates to novel intermediates of the formula:

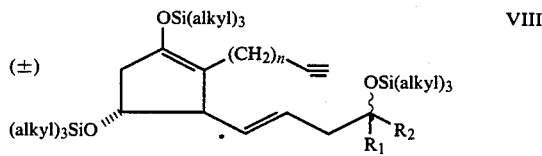

Where n, $R_1$ and $R_2$ are as described above and alkyl relates to alkyl of 1 to 6 carbon atoms inclusive.

Examples of alkyl 1 to 6 carbon atoms, inclusive, are methyl, ethyl, propyl, butyl, pentyl and hexyl and isomeric forms thereof.

Also included in the invention are the individual stereoisomers, and mixtures of the isomers.

Optional bonds are indicated as dashed lines.

Further, alpha configurations are represented by a hatched line, and beta configurations are represented by a solid line, in all formulas.

The specific assay used to detect gastric antisecretory activity is described as follows:

Adult female beagle dogs weighing 13–20 kg are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1N sodium hydroxide to pH 7.0. Following a 30 minute basal secretion the dogs are infused with a saline solution of histamine dihydrochloride at a dose of 1.0 mg/hr. The volume of the diffusion is kept at approximately 13 ml/hr. A steady state plateau of gastric secretion is obtained approximately 1 hour following the start of histamine infusion, at the end of which time the test compound dissolved in an ethanolic iso-osmotic phosphate buffer solution is administered by a single intravenous injection. The duration of the anti-secretory effects is determined and the side-effects, if any, recorded. The compound is rated active if statistically significant inhibition of secretory parameters occur following compound treatment.

Cytoprotective activity is tested as follows. Male, Charles River rats, weighing 180 to 220 g, which are food deprived for 24 hours are administered a test compound. Thirty minutes later, each rat is given 1.0 ml of absolute ethanol intragastrically. The rats are sacrificed sixty minutes after alcohol administration and gastric mucosae are visually examined for the presence of lesions. Objective scoring is based on the presence or absence of lesions and data recorded as the number of rats per group completely protected from lesion formation.

Compounds of this invention were tested as above and found to be antisecretory and cytoprotective. By virtue of these activities, the compounds of Formula VII are useful in treating and alleviating gastric ulcers in mammals.

The compounds of the present invention are formulated into pharmaceutically acceptable dosage forms by conventional methods known to the pharmaceutical art. For example, the compounds can be administered in oral unit dosage forms such as tablets, capsules, pills, powders, or granules. They also may be administered rectally or vaginally in such forms as suppositories or bougies; they may also be introduced in the form of eye drops, intraperitoneally, subcutaneously, or intramuscularly, using forms known to the pharmaceutical art. In general the preferred form of administration is oral.

An effective but non-toxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration and the particular compound employed. An ordinarily skilled physician or veterinarian will readily determine and prescribe the effective amount of the agent to prevent or arrest the progress of the condition. In so proceeding, the physician or veterinarian could employ relatively low dosages at first, subsequently increasing the dose until a maximum response is obtained.

Initial dosages of the compounds of the invention are ordinarily in the area of 0.25 $\mu$g/kg up to at least 50 $\mu$g/kg orally. When other forms of administration are employed equivalent doses are administered.

The compounds of this invention can also be administered as pharmacologically acceptable alkali metal salts such as lithium, sodium and potassium and the like, and hydrates thereof.

The compounds of Formula VIII are useful in preparing compounds of Formula VII.

The compounds of this invention are prepared by the general methods illustrated in the accompanying Charts A through F. Chart A: Furfural, Formula I, reacts with omega-alkynyl magnesium halides, Grignard reagents prepared by methods known to those skilled in the art from omega-haloalk-1-ynes, II, to form the intermediate compounds of Formula III. Where n is greater than 1, the acetylene group of the Grignard is protected by a trialkylsilyl group that can later readily be removed by aqueous potassium fluoride treatment. Where n is 1, R may be hydrogen and no deprotection is necessary to yield compound III. Preferred reaction conditions include addition at ca. 0° of a tetrahydrofuran solution of compound I to a diethyl ether solution of the freshly prepared Grignard reagent. Compounds III are typically purified by distillation at reduced pressure. The intermediates III rearrange upon heating under acidic conditions to form cyclopentenyl compounds of Formula IV. Preferred conditions include heating at ca. 80°-85° in aqueous dioxane containing p-toluenesulfonic acid. Crude compounds IV are typically purified by extraction and column chromatography on silica gel. Compound III further rearranges under acidic or basic conditions to form the isomeric compounds of Formula V. Preferred conditions include treatment of compounds IV with basic Grade III alumina at room temperature. Protection of alcohol intermediates V, using a protecting group ($R_{10}$) such as trialkylsilyl or tetrahydropyranyl by reaction in an inert organic solvent affords the protected derivatives, Formula VI. Preferred reagents and conditions include triethylsilyl chloride and imidazole in dimethylformamide at room temperature. The intermediate compounds VI are typically purified by column chromatography on silica gel.

Chart B: Compounds VI react first with organocopper reagents, Formula XI (prepared by the general method described in U.S. Pat. No. 4,271,314) and then with suitable silylating reagent to form intermediates of Formula XII. Preferred conditions include reaction of VI and XI at ca. −60° in diethyl ether, followed by addition of a trialkyl silyl chloride, preferably with at least one bulky alkyl group (e.g. t-butyldimethylsilyl chloride) which will increase yields and stability, and hexamethylphosphoric triamide, with warming to ca. −20°. After extracting into an organic solvent, such as diethyl ether, and stripping volatiles, the crude intermediates XII are typically purified by column chromatography on silica gel. The acetylenic intermediates XII, after treatment with a strong nonaqueous base in an inert organic solvent, react with dry paraformaldehyde to form isolable intermediates which in turn may be treated with alkyl haloacetates to form intermediates of Formula XIII. Preferred conditions include reaction of XII with butyllithium in tetrahydrofuran at ca. −20°, followed next by addition of paraformaldehyde, and then by addition of alkyl bromoacetates and hexamethylphosphoric triamide. Intermediates XIII are typically purified by column chromatography on silica gel. Hydrolysis of protected compounds XIII under acidic conditions affords acetylenic compounds of this invention, Formula XIV. Preferred hydrolytic conditions include a 3:1:1 mixture of acetic acid/tetrahydrofuran/water stirred at room temperature initially and then warmed to ca. 45°-50°. Acetylenic compounds XIV are typically purified by column chromatography on silica gel.

Analogous alkenyl compounds of this invention, Formula XV, are prepared by catalytic hydrogenation of compounds XIV, using such catalysts as palladium, platinum, ruthenium, and rhodium which have been suitably attenuated or Raney Nickel. Preferred reduction conditions employ hydrogen at atmospheric pressure, cyclohexane/toluene containing quinoline, and 5% palladium/calcium carbonate catalyst. Alkenyl compounds XV are typically purified by column chromatography on silica gel.

An alternative conversion of intermediate XIII to alkenyl compounds XV is illustrated in Chart C: Compound XIII is initially hydrogenated by the general method described in Chart B. Hydrogenation conditions are similar, except that the preferred catalyst is 5% palladium/barium sulfate. Hydrolysis of resultant intermediates, Formula XXI, under acidic conditions affords alkenyl compounds XV. Preferred hydrolytic conditions include a 3:1:1 acetic acid/tetrahydrofuran/water mixture.

The carboxylate function of acetylenic or alkenyl compounds of Formulas XIII and XXI may be reduced to corresponding alcohol functions, as illustrated in Chart D. Reductions are effected with any of various active metal hydrides by methods known to those skilled in the art. Preferred conditions include reaction at ca. 0° with lithium aluminum hydride in diethyl ether. Silyl protecting groups are removed by hydrolysis under acidic conditions, preferably 3:1:1 acetic acid/tetrahydrofuran/water, giving compounds of Formula XXXI. The compounds are typically purified by column chromatography on silica gel.

Charts E and F illustrate methods for preparing hydroxymethylketone analogs from the furan intermediate III (wherein n is 1) described above. (See Chart A.) Chart E: The hydroxyl function of III is protected with an acid-labile group for subsequent reactions. A preferred protecting group is tetrahydropyranyl, added to compounds III by reaction with dihydropyran under acidic conditions by methods known to those skilled in the art. The protected intermediate is converted to acetylenic intermediates XLI by reactions first with paraformaldehyde in strongly basic medium and then with alkyl haloacetates, as described above. (See Chart B.) Corresponding alkenyl intermediates, Formula XLII, are prepared by catalytic reduction of acetylenic compounds XLI, as described above. (See Charts B and C.) A preferred hydrogenation catalyst is 5% palladium/calcium carbonate.

Chart F: Rearrangements of acetylenic or alkenyl compounds, Formulas XLI and XLII, to cyclopentenyl compounds, Formula LI, are effected by the same general methods used to convert compound III to compound V, described above. (See Chart A.) The preferred basic conditions for the second rearrangement, however, employ aqueous sodium carbonate containing a small quantity of hydroquinone. Reaction of intermediates LI with a hindered trialkylsilyl halide, preferably t-butyldimethylsilyl chloride, affords intermediates of Formula LII. The ester function of LII is converted to the hydroxymethylketone function of LIII by the general method described by A. Wissner, *J. Org. Chem.*, 44, 4617 (1979). Intermediates LII, are converted to the corresponding acyl halides, preferably by reaction with oxalyl chloride and dimethylformamide in an inert organic solvent such as dichloromethane. The unisolated acyl halides react with tris(trimethylsilyloxy)ethylene to form unisolated intermediates which, upon heating in acidic medium, hydrolyze and decarboxylate to intermediate alcohols LIII, which are typically purified by column chromatography on silica gel. Silylation of compounds LIII affords protected compounds, Formula LIV. Preferred silylation conditions include reaction of LIII with triethylsilyl chloride in dimethylformamide containing imidazole. Reaction of intermediates LIV with organocopper compounds of Formula XI as described above (See Chart B.), followed by hydrolysis, preferably using 3:1:1 acetic acid/tetrahydrofuran/water as described above (See Chart B.), affords hydroxymethylketone compounds of this invention, Formula LV. Compounds LV are typically purified by column chromatography on silica gel.

DESCRIPTION OF THE PREFERRED EMBODIMENTS

EXAMPLE 1

Preparation of α-(2-propynyl)-2-furanmethanol

Propargyl magnesium bromide was prepared by adding a solution of propargyl bromide (as 145.5 g of 80%, by weight, solution in toluene; 0.976 mole) in 150 ml of diethyl ether to a slurry of 26 g (1.07 mole) of iodine-activated magnesium and 340 mg of mercuric chloride in 450 ml of ether. The rate of addition was adjusted to maintain a vigorous reflux. After addition was complete, the reaction mixture was stirred at room temperature for one hour and then cooled at 0°. A solution of 75 g (0.78 mole) of 2-furancarboxaldehyde in 400 ml of tetrahydrofuran was added dropwise, and the reaction mixture was stirred at room temperature for fifteen minutes, then poured onto a cold saturated ammonium chloride solution and stirred vigorously. The layers were separated and the aqueous layer was extracted with ether. The organic phase was washed with saturated ammonium chloride solution and with brine, dried over sodium sulfate, filtered, and concentrated to dryness. Distillation of the crude material at 1.0 torr gave 100.6 g of the title compound, b.p. 68°–72°. Structure assignment was confirmed by the proton nmr spectrum: 2.05 (t, J=2–3 HZ, ≡C—H), 2.59 (d of d, J=2–3 and 5–6 Hz, —CH₂—C≡), 4.80 (q, J=5–6 Hz, —CHOH—), 6.27 and 7.32 ppm (furan).

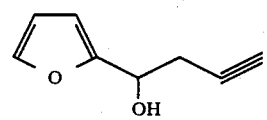

EXAMPLE 2

4-hydroxy-2-(2-propynyl)-2-cyclopenten-1-one

To a solution of 40.2 g (0.295 mole) of the title compound of Example 1 in 800 ml of a 8:1 dioxane/water mixture was added 4 g (0.21 mole) of p-toluenesulfonic acid. The reaction mixture was heated at 83° for 36 hours under argon, cooled, and diluted with 500 ml of ethyl acetate. The organic phase was washed once with water and two times each with 5% sodium bicarbonate solution and brine solution. The aqueous washes were combined and extracted with ethyl acetate. The combined organic phases were dried over sodium sulfate, filtered, and concentrated. Chromatography of the combined crude materials on silica gel (using 25% ethyl acetate in hexane as eluent) gave 12.45 g of the intermediate compound 4-hydroxy-5-(2-propynyl)-2-cyclopenten-1-one as a viscous oil. Structure assignment was confirmed by the proton nmr spectrum.

A solution of 14.5 g (0.11 mole) of the cyclopentenone intermediate in 50 ml of ether was poured into a column packed with 282 g of Grade III alumina (6% water by weight). The column was closed and allowed to stand at room temperature for twenty four hours. The product was eluted from the column with ether and ethyl acetate to give 7.3 g of the title compound as a viscous oil. Structure assignment was confirmed by the proton nmr spectrum:

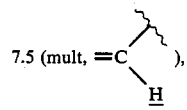

4.98 (—CHOH), 2.16 (t, J=2–3 Hz, ≡C—H), 3.07 ppm (mult, J—CH₂—C≡).

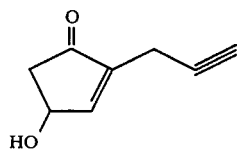

EXAMPLE 3

2-(2-propynyl)-4-[(triethylsilyl)oxy]-2-cyclopenten-1-one

A solution of 250 mg (1.84 mmole) of the title compound of Example 2 in 4 ml of dimethylformamide was treated successively with 200 mg (3 mmole) of imidazole and 300 mg (2 mmole) of triethylsilyl chloride. After stirring for thirty minutes, the reaction mixture was diluted with ether, washed with water, dried over sodium sulfate, filtered, and concentrated to dryness. The crude material was chromatographed on silica gel to give 0.37 g of the title compound as an oil. Structure assignment was confirmed by the proton nmr spectrum: 2.13 (t, J=2 Hz, ≡C—H), 3.08 (mult, —CH₂—C≡), 4.90 (mult, C-11),

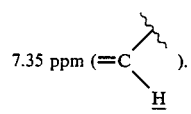

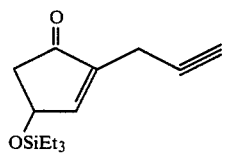

EXAMPLE 4

(1,1-dimethylethyl)dimethyl[[3β-[4-methyl-4-[(trimethylsilyl)oxy]-1E-octenyl]-2-(2-propynyl)-4α-[triethylsilyl)oxy]-1-cyclopenten-1-yl]oxy]silane A solution of 10 g (0.02 mole) trimethyl[1-methyl-1-[3-(tributylstannyl)-2E-propenyl]pentoxy]silane in 25 ml of tetrahydrofuran was cooled to −60° under an argon atmosphere, and 11.8 ml of a 1.7M solution of n-butyllithium is hexane (0.02 mole) was added. The reaction mixture was stirred for forty five minutes, after which a solution of 2.62 g (0.02 mole) of copper-1-pentyne and 6.4 g (0.04 mole) of hexamethylphosphorus triamide in 75 ml of ether was added dropwise. After ten minutes, a solution of 2.4 g (0.01 mole) of the title compound of Example 3 in 20 ml of ether was added, and the reaction mixture was stirred an additional 45 minutes. A solution of 3 g (0.02 mole) of t-butyldimethylsilyl chloride in 15 ml of ether was added, followed by the addition of 25 ml of hexamethylphosphoric triamide. The temperature was allowed to rise to −20°, where it was maintained for one hour. The reaction mixture was poured into 1N hydrochloric acid and ether. The layers were separated and the organic phase was washed with water, dried over sodium sulfate, filtered, and concentrated to dryness. The crude material was chromatographed on silica gel to give 4 g of the title compound as a viscous oil. Structure assignment was confirmed by the proton nmr spectrum: 1.80 (t, J=1-2 Hz, ≡C—H), 4.95-5.80 (mult, C-13, 14), 0.90 ppm (t-Bu).

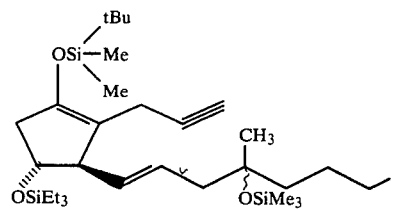

EXAMPLE 5 methyl[[4-[2-[[(1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-2-butynyl]oxy]acetate A solution of 434 mg (0.75 mmole) of the title compound of Example 4 in 5 ml of tetrahydrofuran was cooled to −20° under a nitrogen atmosphere, and 0.49 ml of a 1.7M solution of n-butyllithium in hexane (0.83 mmole) was added. After stirring for one hour at −20°, 27 mg (0.89 mmole) of solid, dried paraformaldehyde was added, and the reaction mixture was warmed to 0°. After stirring for ninety minutes at 0°, the reaction mixture was recooled to −20°, and 147 mg (0.96 mmole) of methyl bromoacetate and 1 ml of hexamethylphosphoric triamide were added. The reaction mixture was stirred at −20° for 75 minutes, then allowed to warm to room temperature before being poured onto 45 ml of water. The product was extracted into ether, which was then washed with brine, dried over sodium sulfate, filtered, and concentrated to dryness. Chromatography of the crude material on silica gel afforded 90.7 mg of the title compound. Structure assignment was confirmed by the proton nmr spectrum: 0.95 (t-Bu), 1.42 (C-16 CH₃), 4.00 (C-11), 4.15 (C-2), 4.25 (C-4), 3.75 ppm (MeO).

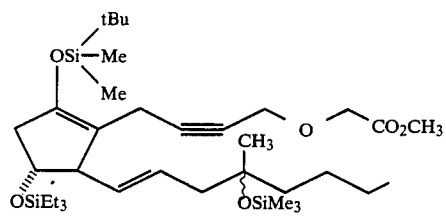

EXAMPLE 6 methyl[[4-[3α-hydroxy-2β-(4-hydroxy-4-methyl-1E-octenyl)-5-oxo-1α-cyclopentyl]-2-butynyl]oxy]acetate A mixture of 106 mg (0.17 mmole) of the title compound of Example 5 in 8 ml of a 3:1:1 solution of acetic acid/tetrahydrofuran/water was stirred at room temperature for four hours and heated at 45°–50° for 1 hour. The reaction mixture was poured onto 80 ml of water and extracted with ether. The organic phase was washed with water, 5% sodium bicarbonate solution, again with water, dried over sodium sulfate, filtered, and concentrated to dryness. The crude material was chromatographed on silica gel to yield 21.3 mg of the title compound as an oil. Structure assignment was confirmed by the proton nmr spectrum: 0.92 (C-20), 1.19 (C-16 CH3), 3.75 (—OCH3), 4.15 (C-2), 4.25 (C-4), 4.00 (mult, C-11), 5.15–6.00 ppm (mult, C-13, 14).

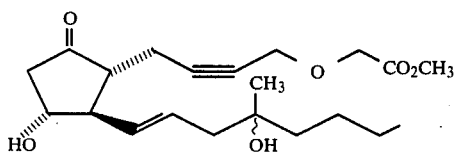

EXAMPLE 7

1,1-dimethylethyl-[[4-[2-[[(1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-2-butynyl]oxy]acetate The title compound was prepared by the method of Example 6 using 611 mg (1.06 mmole) of the title compound of Example 4 in a mixture of 10 ml of tetrahydrofuran, 0.75 ml (1.28 mmole) of n-butyllithium solution, 36 mg (1.19 mmole) of paraformaldehyde, 215 mg (1.10 mmole) of t-butyl bromoacetate and 1 ml of hexamethylphosphoric triamide. Chromatography of the crude material on silica gel gave 151 mg of the pure title compound and 149 mg of slightly impure compound which was used for subsequent reactions without further purification. Structure assignment was confirmed by proton nmr spectrum: 0.92 (Si-t-Bu), 1.48 (-O-t-Bu), 1.18 (C-16 CH3), 4.03 (C-2), 4.23 ppm (C-4).

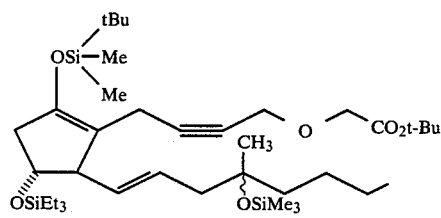

EXAMPLE 8

1,1-dimethylethyl-[[4-[3α-hydroxy-2β-(4-hydroxy-4-methyl-1E-octenyl)-5-oxo-1α-cyclopentyl]-2-butynyl]oxy]acetate The title compound was prepared by the method of Example 6 using 63 mg (0.092 mmole) of the title compound of Example 7 in 2 ml of the 3:1:1 acetic acid/tetrahydrofuran/water solution. An additional 2 ml of the acetic acid/tetrahydrofuran/water solution was added after twenty four hours and the reaction mixture was heated at 45°–50° for one hour. The reaction mixture was concentrated and diluted with ether. The organic phase was washed with water, 5% sodium bicarbonate solution, and water, then dried over sodium sulfate, filtered, and concentrated to dryness. Chromatography of the crude material on silica gel afforded 15 mg of the title compound. Structure assignment was confirmed by the proton nmr spectrum: 0.90 (C-20), 1.15 (C-16 CH3), 1.45 (t-Bu), 3.98 (C-2), 4.20 ppm (C-4).

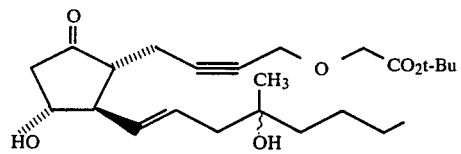

EXAMPLE 9 methyl[[4-[2-[[(1,1-dimethylethyl)dimethylsilyl]oxy]-5β-[4-methyl-4-[trimethylsilyl)oxy]-1E-octenyl]-4α-[(triethylsilyl)oxy]-1-cyclopenten-1-yl]-2Z-butenyl]oxy]acetate A solution of 83 mg (0.13 mmol) of the title compound of Example 5 in 50 ml of toluene, to which had been added 0.95 ml of 5% quinoline in toluene, was hydrogenated at atmospheric pressure and room temperature over 5% palladium/barium sulfate catalyst. After filtration the reaction mixture was concentrated to an oil containing residual quinoline. The title compound exhibited the expected proton nmr spectrum and was used without further purification: 0.89 (Si-t-Bu), 1.15 (C-16 CH3), 3.74 (—OCH3), 4.03 (C-2), 4.15 (C-4), 5.0–5.75 ppm (C-13, 14 and 5,6).

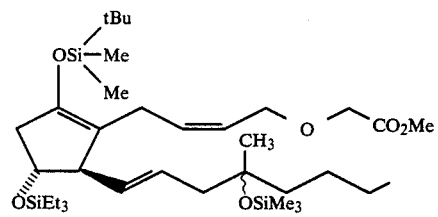

EXAMPLE 10 methyl[[4-[3α-hydroxy-2β-(4-hydroxy-4-methyl-1E-octenyl)-5-oxo-1α-cyclopentyl]-2Z-butenyl]oxy]acetate The title compound was prepared by the method of Example 6 using 97 mg of the title compound of Example 9 (contaminated with quinoline) and 8 ml of a 3:1:1 acetic acid/tetrahydrofuran/water mixture, with stirring at room temperature for 22 hours. The crude material was chromatographed on silica gel to yield 31.8 mg of the title compound as an oil. Structure assignment was confirmed by the proton nmr spectrum: 3.75 (—OCH3), 4.10 (C-2), 1.15 (C-16 CH3), 5.15–6.0 ppm (C-13, 14, and C-5,6).

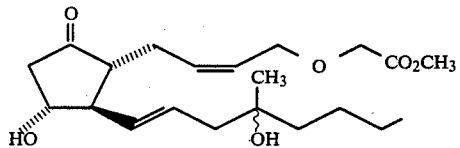

EXAMPLE 11

1,1-dimethylethyl-[[4-[3α-hydroxy-2β-(4-hydroxy-4-methyl-1E-octenyl)-5-oxo-1α-cyclopentyl]-2Z-butenyl]oxy]acetate A solution of 22 mg (0.052 mmole) of the title compound of Example 8 in 3 ml of 1:1 cyclohexane/toluene, to which was added 1.8 ml of 0.1% quinoline in toluene, was hydrogenated at atmospheric pressure at 0° using 5% palladium/calcium carbonate catalyst. After filtration to remove catalyst, the reaction mixture was concentrated to dryness. Chromatography on silica gel yielded 12.6 mg of the title compound as an oil. Structure assignment was confirmed by the proton nmr spectrum: 1.15 (C-16 $CH_3$), 1.45 (t-Bu), 3.93 (C-2), 4.10 (d, J=6 Hz, C-4), 5.15–6.0 ppm (mult, C-13, 14 and C-5, 6).

layers are washed with brine, dried over sodium sulfate, filtered and concentrated to dryness. The residue is chromatographed on silica gel (using ethyl acetate/hexane as eluent) to give the title compound NMR: 2.78 (d of d, J=6, 2.5 Hz, $-CH_2-C\equiv$), 1.92 (t, J=2 Hz, $\equiv CH$), 3.18–4.08 (mult, $-CH_2-O$), 7.49 and 6.33 ppm (furan).

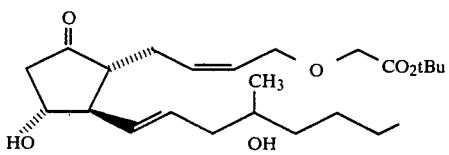

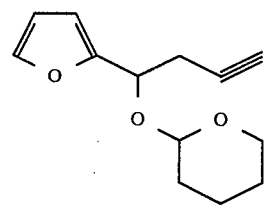

EXAMPLE 12

4α-hydroxy-2α-[4-(2-hydroxyethoxy)-2Z-butenyl]-3β-(4-hydroxy-4-methyl-1E-octenyl)cyclopentanone To a solution of 683 mg of the title compound of Example 9 cooled to 0°, is added 40 mg of lithium aluminum hydride. After 15 minutes at 0°, the reaction mixture is poured into diethyl ether and water. The ether layer is separated and washed with water, dried over sodium sulfate, filtered and concentrated to dryness. The residue is dissolved in 15 ml of a 3:1:1 acetic acid/water/tetrahydrofuran mixture and stirred overnight at room temperature. After diluting the reaction mixture with diethyl ether, it is washed with water, dried over sodium sulfate, filtered and evaporated to dryness. Chromatography of the residue on silica gel (using ethyl acetate as eluent) gives the title compound.

EXAMPLE 15

1,1-dimethylethyl-[[5-(2-furanyl)-5-[(tetrahydro-2H-pyran-2-yl)oxy]-2-pentynyl]oxy]acetate The title compound is prepared by the method of Example 5 using 1 g of the title compound of Example 14 in 10 ml of tetrahydrofuran, one equivalent of n-butyllithium, 0.16 g of paraformaldehyde, 1 ml of hexamethylphosphoric triamide, and 1.06 g of t-butyl bromoacetate.

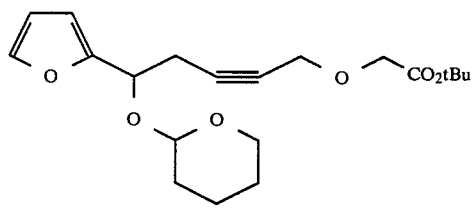

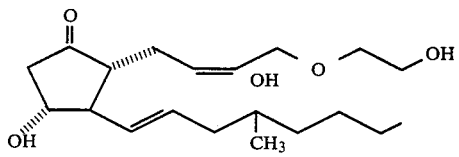

EXAMPLE 13

4α-hydroxy-2α-[4-(2-hydroxyethoxy)-2-butynyl]-3β-(4-hydroxy-4-methyl-1E-octenyl)cyclopentanone The title compound is prepared by the method of Example 12 using 68 mg of the title compound of Example 5 as starting material.

EXAMPLE 16

1,1-dimethylethyl[[5-(2-furanyl)-5-[(tetrahydro-2H-pyran-2-yl)oxy]-2Z-pentenyl]oxy]acetate The title compound is prepared by the method of Example 11 using 1 g of the title compound from Example 15 and 150 mg of 5% palladium/calcium carbonate catalyst.

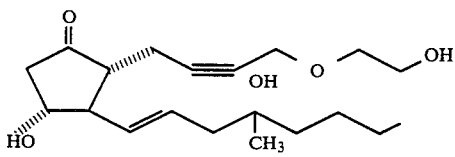

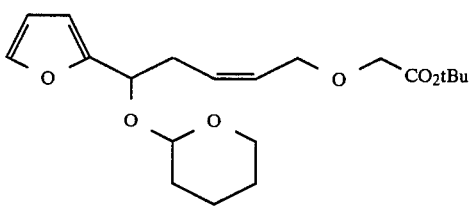

EXAMPLE 14

2-[1-(2-furanyl)-3-butynyloxy]tetrahydro-2H-pyran

To a solution of 10 g (0.073 mole) of the title compound of Example 1 in 40 ml of tetrahydrofuran is added 10 g (0.12 mole) of dihydropyran and 100 mg of p-toluenesulfonic acid monohydrate. The reaction mixture is stirred at room temperature for 4 hours, then diluted with water and 5 ml of 5% aqueous sodium hydroxide. After removal of the solvent, the residue is extracted three times with diethyl ether. The organic

EXAMPLE 17

[[4-(3-hydroxy-5-oxo-1-cyclopenten-1-yl)-2-butynyl]oxy]acetic acid

The title commpound is prepared by the method of Example 2 using 1 g of the title compound of Example 15, with the exception that the intermediate cyclopentenone is rearranged using aqueous sodium carbonate solution (pH 10–11) containing 1% hydroquinone. After stirring for 24 hours at room temperature, the reaction mixture is acidified to pH 2-3 with dilute hydrochloric acid and extracted with ether. The combined extracts are washed with brine, dried over sodium sulfate, filtered, and concentrated to dryness. The residue is chromatographed on Biosil A (using ethyl acetate/hexane as eluent) to afford the title compound.

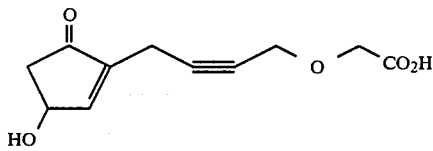

EXAMPLE 18

4-[(triethylsilyl)oxy]-2-[4-[2-oxo-3-[(triethylsilyl)oxy]-propoxy]-2-butynyl]-2-cyclopenten-1-one A solution of 500 mg of the title compound from Example 17 and 600 mg of imidazole in 8 to 10 ml of dimethylformamide is treated at room temperature with 800 mg of t-butyldimethylsilyl chloride. After 1 hour, the reaction mixture is poured into a mixture of hexane/ether (1:1) and water. The organic layer is washed with water three times, dried over sodium sulfate and concentrated in vacuo. Chromatagraphy on silica gel (using 10% ethyl acetate/hexane as eluent) yields the intermediate product, a bis silyl ether.

A solution of 600 mg of the silyl ether in 5 ml of methylene chloride cooled to 0° is treated with 2-3 drops of dimethylformamide and then with a solution of 200 mg of oxalyl chloride in one ml of methylene chloride. The reaction mixture is allowed to warm to room temperature and after one hour the solution is blown to dryness. The residue is dissolved in 6 ml of chlorobenzene, treated with 700 mg of tris(trimethylsilyloxy)ethylene prepared as described by A. Wissner, *J. Org. Chem.*, 44, 4617 (1979), and refluxed under argon for 3 to 4 hours. The mixture is cooled, concentrated to a paste which is dissolved in 3 to 4 ml of tetrahydrofuran, and treated with one ml of 1N hydrochloric acid. After refluxing under argon for one hour, the solution is cooled, diluted with ethyl acetate, and washed with brine solution. The aqueous wash is extracted twice with chloroform and the combined extracts are dried over sodium sulfate, filtered and concentrated to dryness. Chromatography of the residue on silica gel (using 80% ethyl acetate/20% hexane as eluent) gives an oil.

The oil (110 mg) is dissolved in 2 ml of dimethylformamide containing 150 mg of imidazole and then is treated with 150 mg of triethylsilyl chloride. The reaction mixture is stirred at room temperature for one hour and is diluted with diethyl ether, washed with water three times, and then dried over sodium sulfate. Filtration and removal of the solvent gives the title compound.

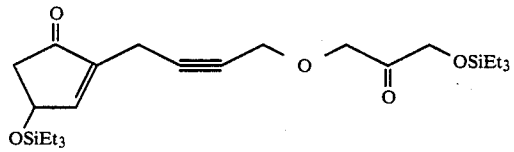

EXAMPLE 19

4α-hydroxy-3β-(4-hydroxy-4-methyl-1E-octenyl)-2α-[4-(3-hydroxy-2-oxopropoxy)-2-butynyl]cyclopentanone The title compound is prepared by the methods of Examples 4 and 6 using 500 mg of the title compound of Example 18, except that the copper enolate is not trapped with t-butyldimethylsilyl chloride but is worked up directly.

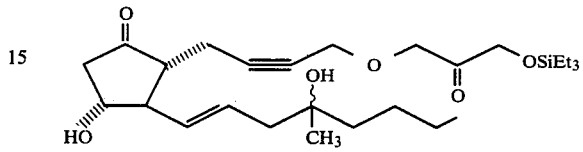

EXAMPLE 20

[[4-(3-hydroxy-5-oxo-1-cyclopenten-1-yl)-2Z-butenyl]oxy]acetic acid

The title compound is prepared by the method of Example 17 using 1 g of the title compound of Example 16.

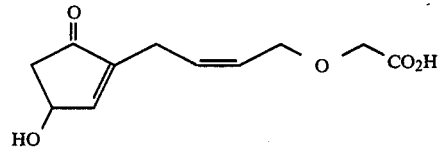

EXAMPLE 21

4-[(triethylsilyl)oxy]-2-[4-[2-oxo-3-[(triethylsilyl)oxy]-propoxy]-2Z-butenyl]-2-cyclopenten-1-one The title compound is prepared by the method of Example 18 using 500 mg of the product from Example 20.

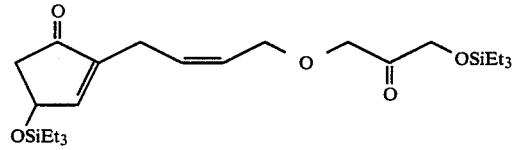

EXAMPLE 22

4α-hydroxy-3β-(4-hydroxy-4-methyl-1E-octenyl)-2α-[4-(3-hydroxy-2-oxopropoxy)-2Z-butenyl]cyclopentanone The title compound is prepared by the method of Examples 4 and 6 using 500 mg of the product from Example 21.

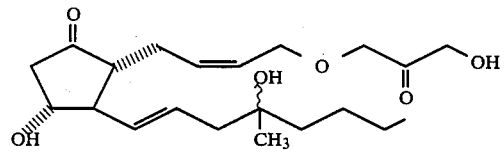

CHART A
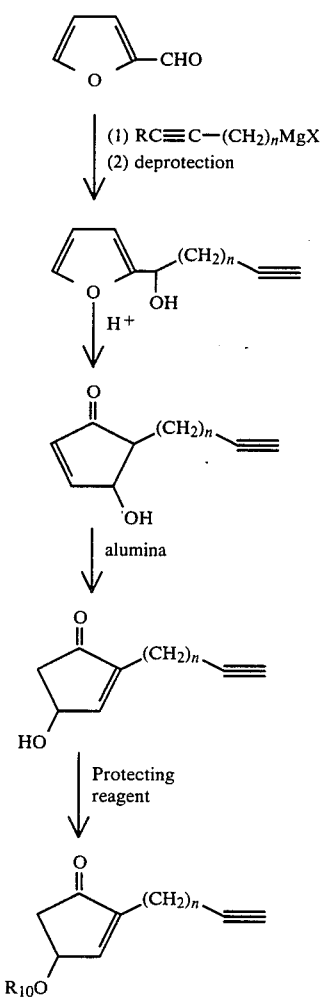
CHART B
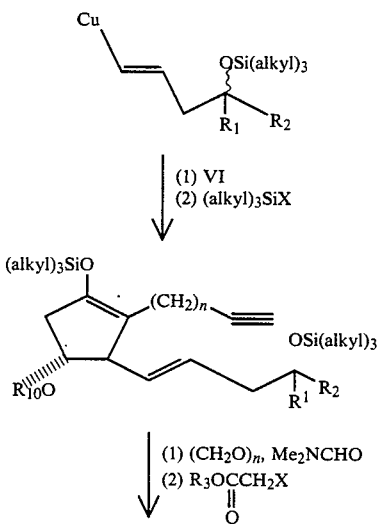
CHART B -continued
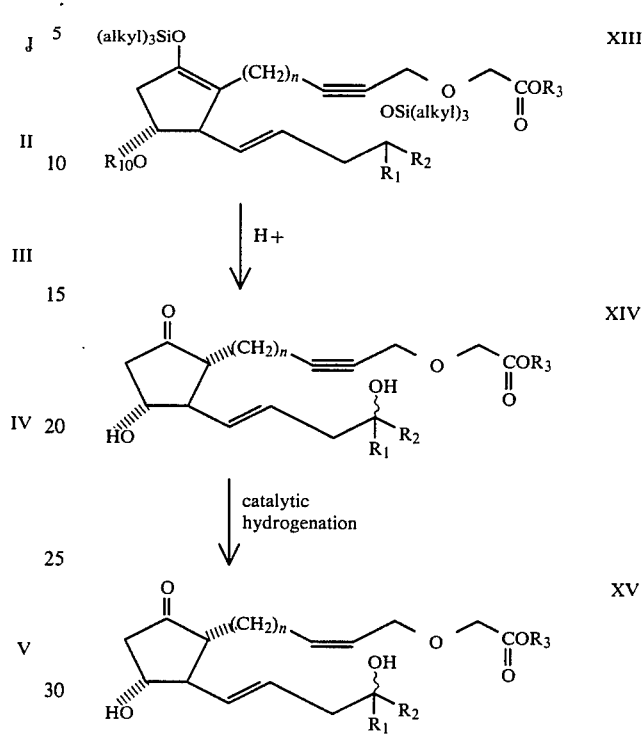
CHART C
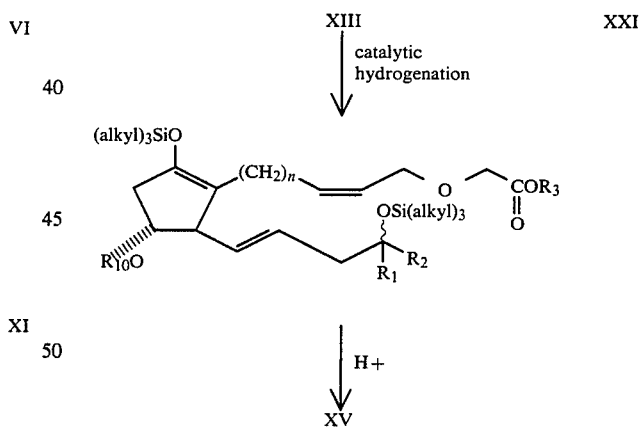
CHART D
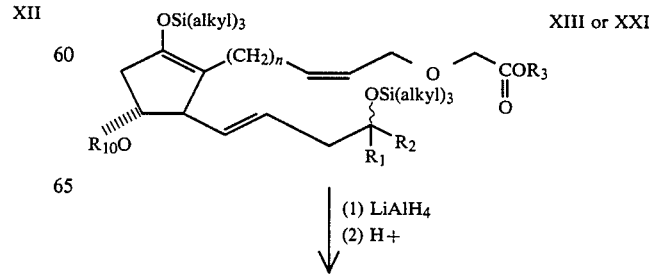

CHART D

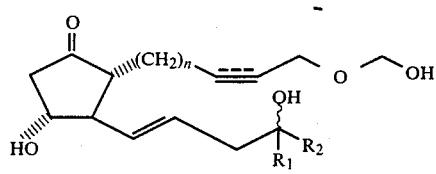

CHART E

III (n = 1)

(1) 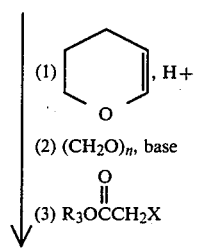, H+

(2) (CH₂O)ₙ, base (3) R₃OCCH₂X
       ‖
       O

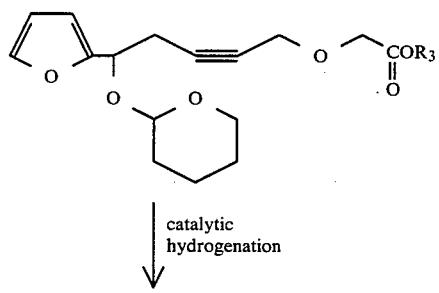

catalytic hydrogenation

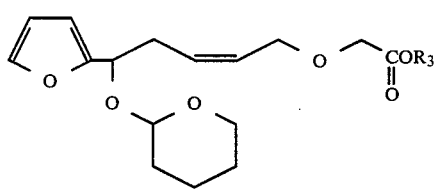

XLI or XLII

CHART F

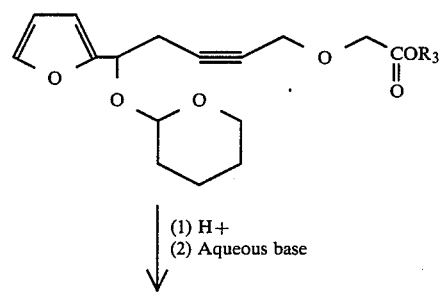

(1) H+
(2) Aqueous base

CHART F —continued

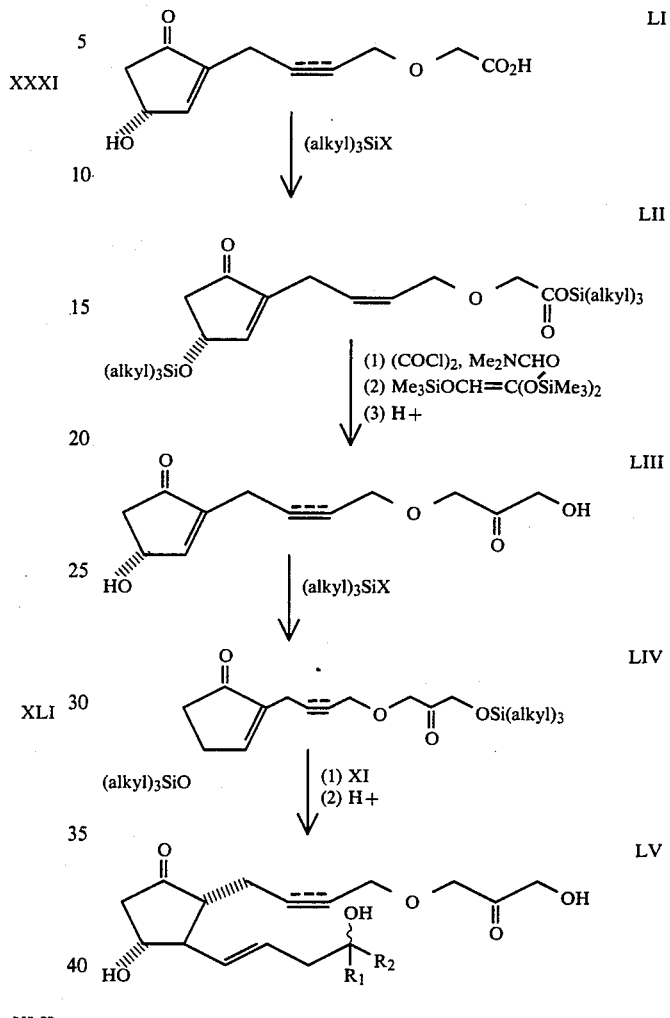

What is claimed is:

1. An Intermediate compound of the formula:

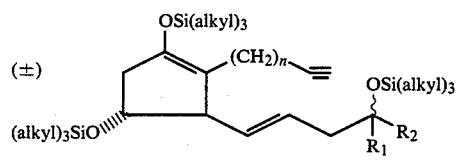

wherein n is an integer of from 1 to 6 inclusive, wherein R₁ is:
(a) hydrogen;
(b) alkyl of 1 to 6 carbon atoms, inclusive;
(c) trifluoromethyl;
(d) trichloromethyl;
(e) alkenyl; or
(f) alkynyl;
wherein R₂ is straight chain alkyl of 1 to 6 carbon atoms inclusive.

2. (1,1-Dimethylethyl)dimethyl[[3β[4-methyl-4-[(trimethylsilyl)oxy]-1E-octenyl]-2-(2-propynyl)-4α-[(triethylsilyl)oxy]-1-cyclopenten-1-yl]oxy]silane, a compound according to claim 1.

* * * * *